(12) United States Patent
Hunig (10) Patent No.: US 8,334,102 B2
(45) Date of Patent: Dec. 18, 2012

(54) HUMAN CD28 SPECIFIC MONOCLONAL ANTIBODIES FOR ANTIGEN-NONSPECIFIC ACTIVATION OF T-LYMPHOCYTES

(75) Inventor: Thomas Hunig, Wurzburg (DE)

(73) Assignee: Theramab LLC, Moscow (RU)

( * ) Notice: Subject to any disclaimer, the term of this patent is extended or adjusted under 35 U.S.C. 154(b) by 0 days.

(21) Appl. No.: 12/756,665

(22) Filed: Apr. 8, 2010

(65) Prior Publication Data

US 2011/0009602 A1 Jan. 13, 2011

Related U.S. Application Data

(60) Continuation of application No. 11/019,530, filed on Dec. 23, 2004, now abandoned, which is a division of application No. 09/449,077, filed on Nov. 24, 1999, now Pat. No. 6,987,171, which is a continuation of application No. PCT/DE98/01499, filed on May 28, 1998.

(30) Foreign Application Priority Data

May 28, 1997 (DE) .................................. 197 22 888

(51) Int. Cl.
*G01N 33/53* (2006.01)
(52) U.S. Cl. ........................................................ 435/7.1
(58) Field of Classification Search ........................ None
See application file for complete search history.

(56) References Cited

U.S. PATENT DOCUMENTS 6,987,171 B1 1/2006 Hunig

OTHER PUBLICATIONS

Nature, 2006, vol. 440, pp. 388-389.*
Nature, 2006, vol. 440, pp. 855-856.*
Damle, et al., J. Immunol., Mar. 1988, 140: 1753-1761.
Scalzo, A.A., et al., "Induction of Protective Cytotoxic T Cells to Murine Cytomegalovirus by Using a Nonapeptide and a Human-Compatible Adjuvant (Montanide ISA 720)," J. of Virology, vol. 69, No. 2, Feb. 1995, 1306-1309.
ATCC Patent Depository Receipt—ATCC® No. 98795™—U.S. Patent No. 6,914,123, downloaded Jul. 21, 2009, 1 page.
MC1061—EcoliWiki, Alternate Names, downloaded Jul. 20, 2009, 1 page.
L929—Horst Ibelgaufts' COPE: Cytokines & Cells Online Pathfinder Encyclopaedia, downloaded Jul. 20, 2009, 4 pages, www.copewithcytokines.de/cope.cgi?key-L929.
Fujimura, A.E., "DNA Sequences Encoding CD4$^+$ and CD8$^+$ T-Cell Epitopes Are Important for Efficient Protective Immunity Induced by DNA Vaccination with a *Trypanosoma cruzi* Gene," Infection and Immunity, vol. 69, No. 9, Sep. 2001, p. 5477-5486.

* cited by examiner

*Primary Examiner* — Ilia Ouspenski
(74) *Attorney, Agent, or Firm* — Millen, White, Zelano, Branigan, P.C.

(57) ABSTRACT

The invention teaches human-compatible monoclonal antibodies which are specific against human CD28 and human T-lymphocytes of several to all subgroups to activate without occupancy of an antigen receptor of the human T-lymphocytes and thus antigen-non-specifically.

1 Claim, 14 Drawing Sheets

HUMAN CD28 SPECIFIC MONOCLONAL ANTIBODIES FOR ANTIGEN-NONSPECIFIC ACTIVATION OF T-LYMPHOCYTES

This application is a continuation of U.S. patent application Ser. No. 11/019,530, filed Dec. 23, 2004, now abandoned which is a divisional of U.S. patent application Ser. No. 09/449,077, filed Nov. 24, 1999, now U.S. Pat. No. 6,987, 171, which is a continuation of International Patent application PCT/DE98/01499, filed May 28, 1998.

The invention in question is concerned with monoclonal antibodies which are specific for human CD28 and activate T-lymphocytes without occupancy of an antigen receptor of the T-lymphocytes, i.e. antigen-non-specific, hybridoma cells for the production of such antibodies, a procedure for the production of such antibodies and applications of such antibodies. Monoclonal antibodies is the term for antibodies which are produced by hybrid cell lines (so-called hybridoma), which have resulted from a fusion of a B cell of animal or human origin producing antibodies with a suitable myelom tumour cell. CD28 designates a cell surface module of a known amino-acid sequence expressed on T-lymphocytes of human and animal origin, to which the abbreviation CD28 was given in the course of the international "Human Leukocyte Typing Workshops". With the activation of T-lymphocytes, an increase in metabolic activity, enlargement of the cell volume, synthesis of immunologically important molecules and the start of cell division (proliferation) of T-lymphocytes upon an external stimulus is meant. For example, these processes are initiated by the occupancy of the CD28 molecule on T cells by certain CD28-specific monoclonal antibodies. The activation of T-lymphocytes with the peripheral phenomena described is a part of the physiological immune reaction, but can get out of control there (lymphoproliferative diseases) or be insufficient (immune deficiency) in pathological situations.

To start with, the following technological background is necessary in order to understand the invention. The activation of resting T cells for proliferation and functional differentiation firstly demands the occupancy of two surface structures, so-called receptors: 1. the antigen receptor, which possesses a differing specificity from cell to cell and is necessary for the recognition of antigens, e.g. viral fission products; and the CD28 molecule expressed on all resting T cells to the same extent, which naturally binds on ligands on the surface of other cells of the immune system. We talk of the "co-stimulation" of the antigen-specific immune reaction through CD28. In cell cultures, these processes can be imitated by occupying the antigen receptor and the CD28 molecule with suitable monoclonal antibodies. In the classical system of co-stimulation, neither the occupancy of the antigen receptor nor that of the CD28 molecule alone leads to T cell proliferation, whereas the occupancy of both receptors is effective. This observation was made on T cells in man, mice and rats.

Monoclonal antibodies of the kind stated at the beginning are known. A "direct" activation of resting T-lymphocytes by CD28-specific monoclonal antibodies, i.e. activation independent of the occupancy of the antigen receptor, has been observed in the following systems: in the literature Brinkmann et al., J. Immunology, 1996, 156, 4100-4106, it was shown that a very small fraction (5%) of human T-lymphocytes bearing the surface marker CD45 R0, which is typical for resting T-lymphocytes, is activated by the "classical" CD28-specific monoclonal antibody 9.3 with addition of the growth factor Interleukin-2 (IL-2) without the occupancy of the antigen receptor. In the work by Siefken et al., Cellular Immunology, 1997, 176: 59-65, it was shown that a CD28-specific monoclonal antibody produced by conventional means, i.e. by immunisation of mice with human T cells, can activate a sub-group of human T cells in cell culture without occupancy of the antigen receptor for proliferation if CD28 is occupied by this monoclonal antibody and the cell-bound monoclonal antibody molecules are additionally crosslinked with one another by further antibodies. In both cases, the antibodies described are firstly not principally suited for use in human medicine, as they are mouse antibodies. Further, the two described antibodies have the common point that only a very small part of the T cells can be activated "directly".

In the work by Tacke et al., Eur. J. Immunol., 1997, 27:239-247, two kinds of CD28-specific monoclonal antibodies with varying functional properties were described: "classical antibodies", which only co-stimulate the activation of resting T cells with the simultaneous occupancy of the antigen receptor; and "direct" ones, which can activate T-lymphocytes of all classes in vitro and in animals to proliferation without occupancy of the antigen receptor. Both monoclonal antibodies known in this regard come from an immunisation with cells on which rat CD28 is expressed and are available by various selections aimed at the properties described for each of them. Further, this literature shows that CD28-specific monoclonal antibodies possessing the directly activating effect bind on T-lymphocytes much more slowly than classical CD28-specific monoclonal antibodies; the binding on a mouse fibroblast cell line (L-929), on the surface of which the CD28 molecule is artificially expressed by transfection, takes place for classical and "directly" stimulating CD28-specific monoclonal antibodies at the same speed. From this, it is deduced that the "directly" stimulating CD28-specific monoclonal antibodies known in this regard recognise an active form of the CD28 molecule, the existence on which on resting T cells is suppressed by a mechanism as yet unknown, but which is accessible in expression of the molecule in non-T tumour cell lines. However, the monoclonal antibodies known in this regard are on the one hand specific against rat CD28, on the other hand mouse antibodies. They are therefore not suitable for therapeutic purposes in man for both reasons.

Compared with the state of the art as per the first two pieces of literature stated, the invention in question is based on the technical problem of making "direct" human-CD28 specific monoclonal antibodies available which on the one hand are human-compatible and on the other hand are able to activate human T cells to a large extent.

As a solution to this technical problem, the invention in question teaches human-compatible monoclonal antibodies which are specific for human CD28 and human T-lymphocytes of several to all sub-groups to activate without occupancy of an antigen receptor of the human T-lymphocytes and thus antigen-non-specifically, preferably with human constant components. Constant components of an antibody are areas which are not of importance for the recognition of an antigen, as opposed to the variable areas, which define the antigen-specificity of an antibody. Constant components however differ in antibodies of various kinds and consequently also animals and humans. The constant areas of an antibody must correspond to those of antibodies of an organism which is to be treated with the antibodies in order to be compatible. Monoclonal antibodies in accordance with the invention are therefore human-compatible on the one hand, be it per se or by humanisation, and can on the other hand be used to treat various diseases which are based on an excessively low T-lymphocyte activity, as the antibodies are specific against human CD28 and as the activation of the T-lymphocytes is extensive.

The invention in question naturally includes various derivatives of monoclonal antibodies provided the features stated in the claims are fulfilled. Derivatives of monoclonal antibodies means modifications of the monoclonal antibodies which are generated by customary biochemical or gene-technical manipulations. This exists, for example, in the humanisation of monoclonal antibodies of a mouse through partial substitution of structural (constant) components of the mouse antibody through those of a human one.

In detail, monoclonal antibodies according to the invention are available through: A) production of hybridoma cells enabled to produce monoclonal human-CD28 specific animal antibodies by means of an immunisation with non-T tumour cell lines on which human CD28 is expressed, B) if applicable, humanisation of the monoclonal animal antibodies available from the hybridoma cells pursuant to phase A through a biochemical or gene-technological exchange of constant components of the animal antibodies against analogous constant components of a human antibody or replacement of genes of the hybridoma cells corresponding to the components; C) secreting of the antibodies in hybridoma cell cultures and isolation of the antibodies from it or production of the antibodies by injection of the hybridoma cells into animals, for example mice, and isolation of the antibodies from the body fluid of the animal. Accordingly, compared with the nearest places in literature, Brinkmann et al., J. Immunology, 1996, 156, 4100-4106, and Siefken et al., Cellular Immunology, 1997, 176: 59-65, the core of the invention entails the knowledge that a "direct" activation of practically all the T-lymphocytes can be achieved if the monoclonal antibodies are obtained by immunisation with non-T tumour cells on which human CD28 is expressed instead of an immunisation with T cell lines. In this way, monoclonal antibodies can be obtained which are not only specific against human CD28, but also cause a "direct" activation to a considerable extent. In detail, monoclonal antibodies according to the invention have specificity for determinants of the human CD28 molecule, which are difficult to access on the naturally expressed CD28 molecule and the occupancy of which by the new kind of monoclonal antibodies leads to an activation of the T cells. A determinant means the area of a molecule which is defined by the binding specificity of one or more antibodies.

The principal mode of procedure in the production of hybridoma cells, in humanisation and in the production of monoclonal antibodies from (humanised) hybridoma cells is well known to experts and need not be explained in any more detail here. As a matter of principle, all the customary, known and freely available cell lines, in particular for the production of the hybridoma cells, can be used here. For the production of the monoclonal antibodies, not only the mode of procedure described below, but also recombinant expression, which is known in detail to experts, is to be considered.

In detail, it is preferable if the hybridoma cells enabled to produce monoclonal human-CD28 specific animal antibodies are available through a) creation of a plasmid by means of insertion of human-CD28 cDNA into the pHOAPr-1-neo vector following excision of the SaII-HindIII fragment and production of protoplasts from *Escherichia coli* (MC1061) which carry the plasmid, b) fusing of the protoplasts with mouse A20J and/or L929 tumour cells by means of polyethylene glycol, c) cultivation of the transfected cells received in phase b, d) screening of the transfected mouse A20J and/or L929 cells for the expression of human CD28 and selection of mouse A20J and/or L929 cells expressing human-CD28, e) immunisation of BALB/c mice with mouse A20J and/or L929 cells expressing human-CD28 (for example by injection 6.times.i.p. and then 1.times.i.v.), f) removal of spleen cells of the mice immunised in this way and fusing the spleen cells with non-producer cells of the cell line X63-Ag 8.653 (i.e. not producing any antibodies) by means of polyethylene glycol, g) selection of the hybridoma cells obtained in this way with the condition that in the supernatant of selected hybridoma cells there are antibodies contained which bind on human CD28 expressing mouse A20J and/or L929 cells and h) cultivation/sub-cloning of the selected hybridoma cells obtained in phase g. Naturally, other expression systems known to the experts could be used instead of phases a) to d). Human-CD28 cDNA is freely available from Dr. A. Aruffo and Dr. B. Seed, who published the sequence and also the following part of literature: Aruffo, A., and Seed, B., 1987, "Molecular cloning of a CD28 cDNA by a high efficiency COS cell expression system", Proc. Natl. Acad. Sci. USA, 84:8573. Therefore, the production of the human CD28 cDNA can be seen in detail from this literature. In addition, each expert can very simply and quickly produce a human-CD28 cDNA clone with the help of the sequence deposited in the gene bank and the polymerase chain reaction. The pH.beta.APr-1-neo vector is freely available from the authors of the literature Gunning, P., et al., 1987, "A human .beta.-actin expression vector system directs high-level accumulation of antisense transcripts", Proc. Natl. Acad. Sci. USA, 84:4831. In this. "neo" stands for neomycin resistance. Phase c) is therefore carried out with the presence of neomycin. The cell lines and/or micro-organisms mentioned above are freely available and can be purchased from the American Type Culture Collection (ATCC). With regard to *Escherichia coli* (MC1061), supplementary reference is made to the literature Meissner, P. S., et al., 1987, "Bacteriophage gamma cloning system for the construction of directional cDNA libraries", Proc. Natl. Acad. Sci. USA, 84:4171.

Accordingly, the object of the invention also includes, hybridoma cells as well as a procedure for the production of antibodies.

However, within the framework of the invention, the use of monoclonal antibodies according to the invention for the production of medicines, in particular the treatment of diseases with pathologically reduced CD4-T cell figures, such as AIDS or in stem cell transplantations following chemotherapy of leukemic diseases, for potentiating and/or qualitative influence of immune reactions in protective inoculations and/or in order to influence the quality of T cell reactions, in particular to influence the production of various effector molecules, for example cytokines and chemokines and their receptors, e.g. in auto-immune diseases and AIDS, is of independent importance. The galenic production of the medicines for the various forms of administration is well known to experts and need not be explained in more detail here. The quality of the T cell reaction is in particular to be understood as the production of certain cytokine patterns, which can, for example, be effective in a pro or anti-inflammatory way or can selectively lead to the production of certain classes of immunoglobulin in B lymphocytes (classic examples of differing qualities of the T cell reaction are the function TH1 and TH2 phenotypes, as described below in examples), The invention also entails procedures for the healing of the diseases mentioned both above and below, making use of monoclonal antibodies according to the invention.

Below, the invention is explained in more detail on the basis of examples of implementation. In particular, the production of monoclonal antibodies according to the invention is described. In these examples, screening procedures with which monoclonal antibodies according to the invention and hybridoma cells used as a basis can be selected also become clear in detail. Therapeutic possibilities of use according to the invention also become clear in the following examples.

The experiments portrayed and the examples of the effects of "direct" CD28-specific monoclonal antibodies were carried out in the animal model of rats, with the monoclonal antibody JJ319 being used as an example of a "classical" CD28-specific antibody, the monoclonal antibody JJ316 being used as an example of a "directly" activating one. Both antibodies are freely available and can be purchased from the firm of Pharmingen, San Diego, USA. JJ319 and JJ316 antibodies are also available in accordance with literature, M. Tack et al., Immunology, 1995, 154: 5121-5127, to which reference is hereby expressly made, also with regard to details of the production of hybridoma cells and monoclonal antibodies.

EXAMPLE 1

In this example, the production of monoclonal antibodies according to the invention, i.e. human CD28-specific, is described. They are also termed below as CMY-2. Human CD28 from a cDNA library was recombinantly expressed in A20J and/or L929 cell lines. To start with, a plasmid was created by means of insertion of human-DC28 cDNA into the pH.beta.APr-1-neo vector following excision of the SalI-HindIII fragment. Protoplasts, which carry the plasmid, were produced from *Escherichia coli* (MC1061). There was then a fusing of the protoplasts with mouse A20J and/or L929 tumour cells by means of polyethylene glycol. The transfected cells obtained in this way were cultivated in the customary way. There was then a screening of the transfected mouse A20J and/or L929 cells for expression of human-CD28 and selection of mouse A20J and/or L929 cells expressing human-CD28.

Proof of the successful expression was done with the help of a conventional, commercially available fluorescence-marked antibody with specificity for human CD28 (9.3-phycoerythrin). As a negative check, non-transfected A20J or L929 cells were stained with the same antibody. The transfectants (A20J-CD28 and L929-CD28) showed a higher fluorescence intensity. As not all the cells were CD28 positive, CD28 positive cells were sub-cloned and used for immunisation. As can be seen in FIG. 1 from the displacement of the clouds of dots to the top in the two right-hand diagrams, these cells reacted with the purchased antibody, i.e. expressed human CD28 on their surface.

The A20J human-CD28 cell line was used for the immunisation of BALB/C mice. Cell fusion and screening were carried out as follows: i) immunisation of BALB/c mice with the mouse A20J cells expressing the human-CD28 (injections 6.times.i.p. and then 1.times.i.v.). ii) Removal of spleen cells of the mice immunised in this way and fusing of the spleen cells with cells of the X63-Ag 8.653 cell line by means of polyethylene glycol. iii) Selection of the hybridoma cells obtained in this way with the condition that in the supernatant of selected hybridoma cells there are antibodies contained which bind on mouse A20J and/or L929 cells expressing human-CD28.

Figure 1A:
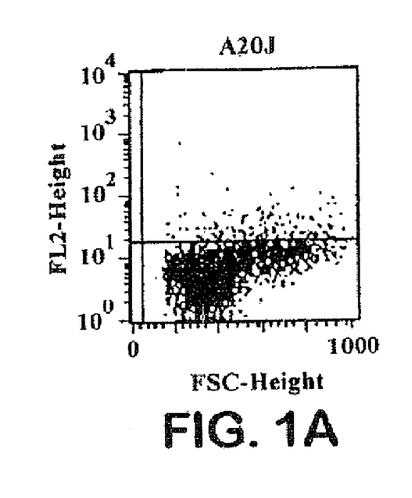
FIGS. 1A-1D show expression data.
Figure 1B:
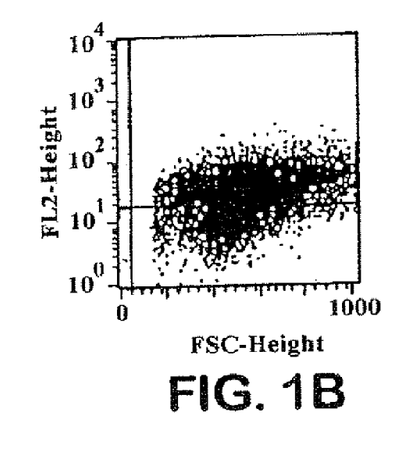
Figure 1C:
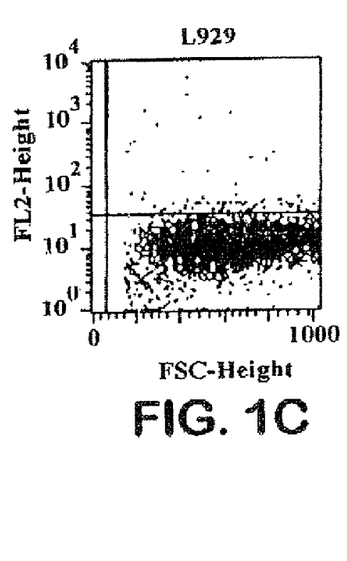
Figure 1D:
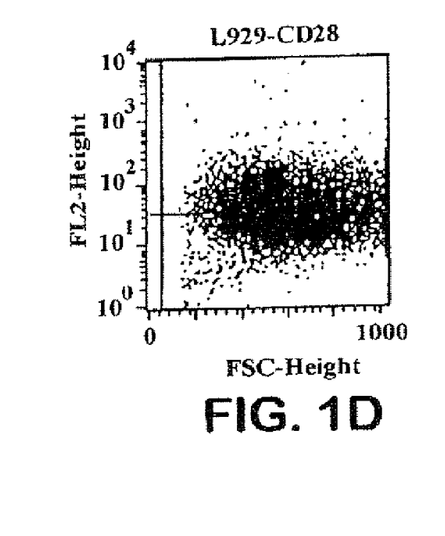
Figure 2A:
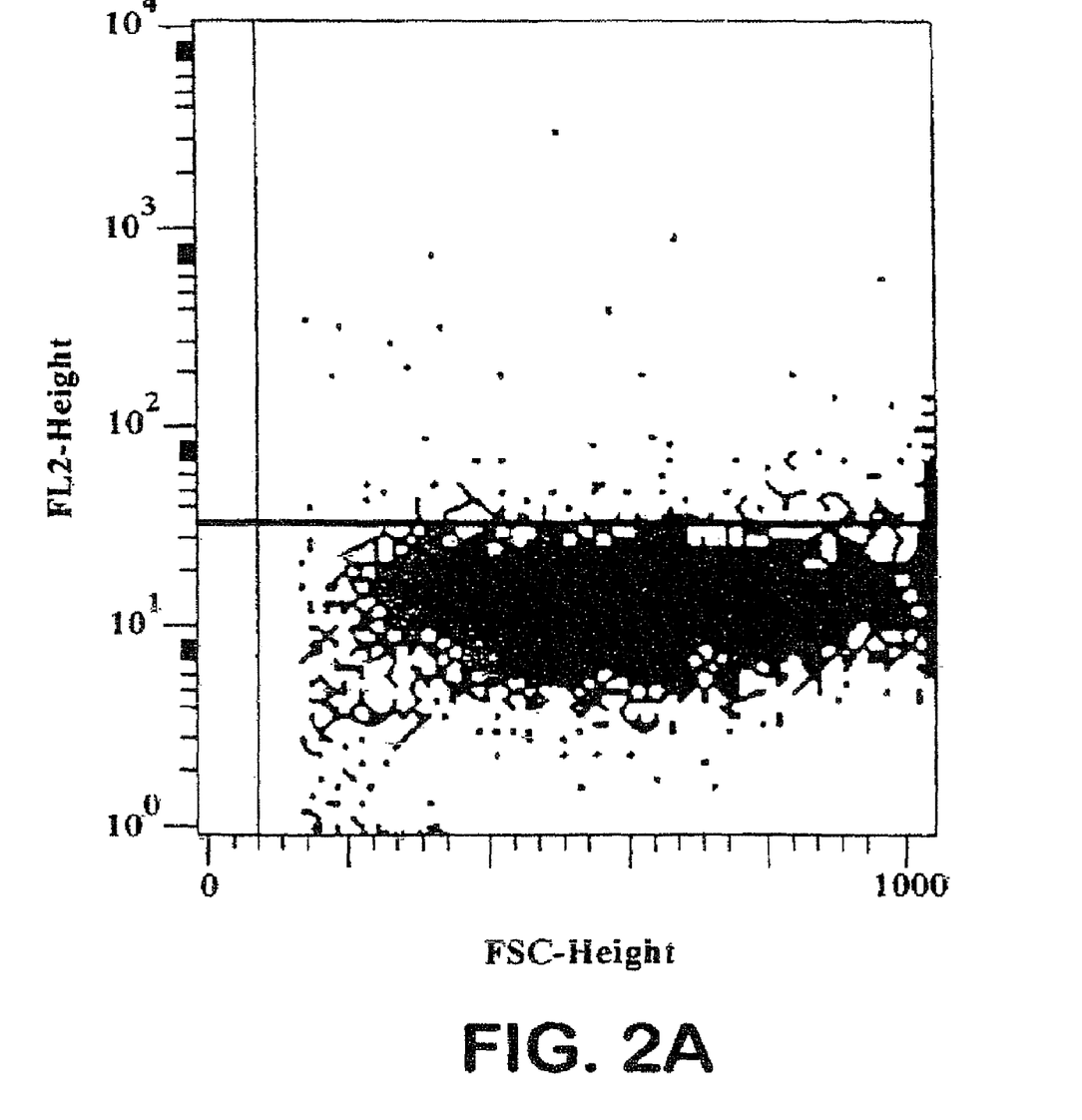
FIGS. 2A-2C show staining data.
Figure 2B:
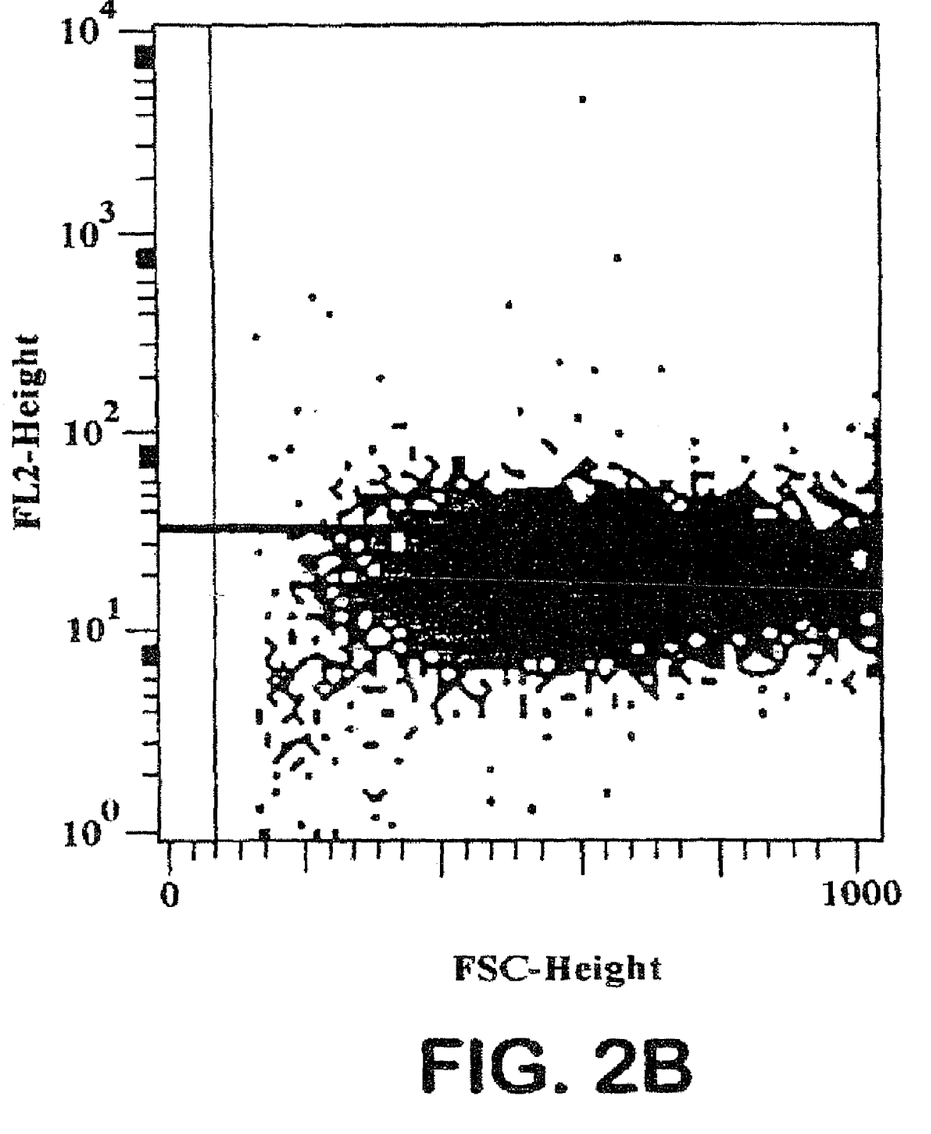
Figure 2C:
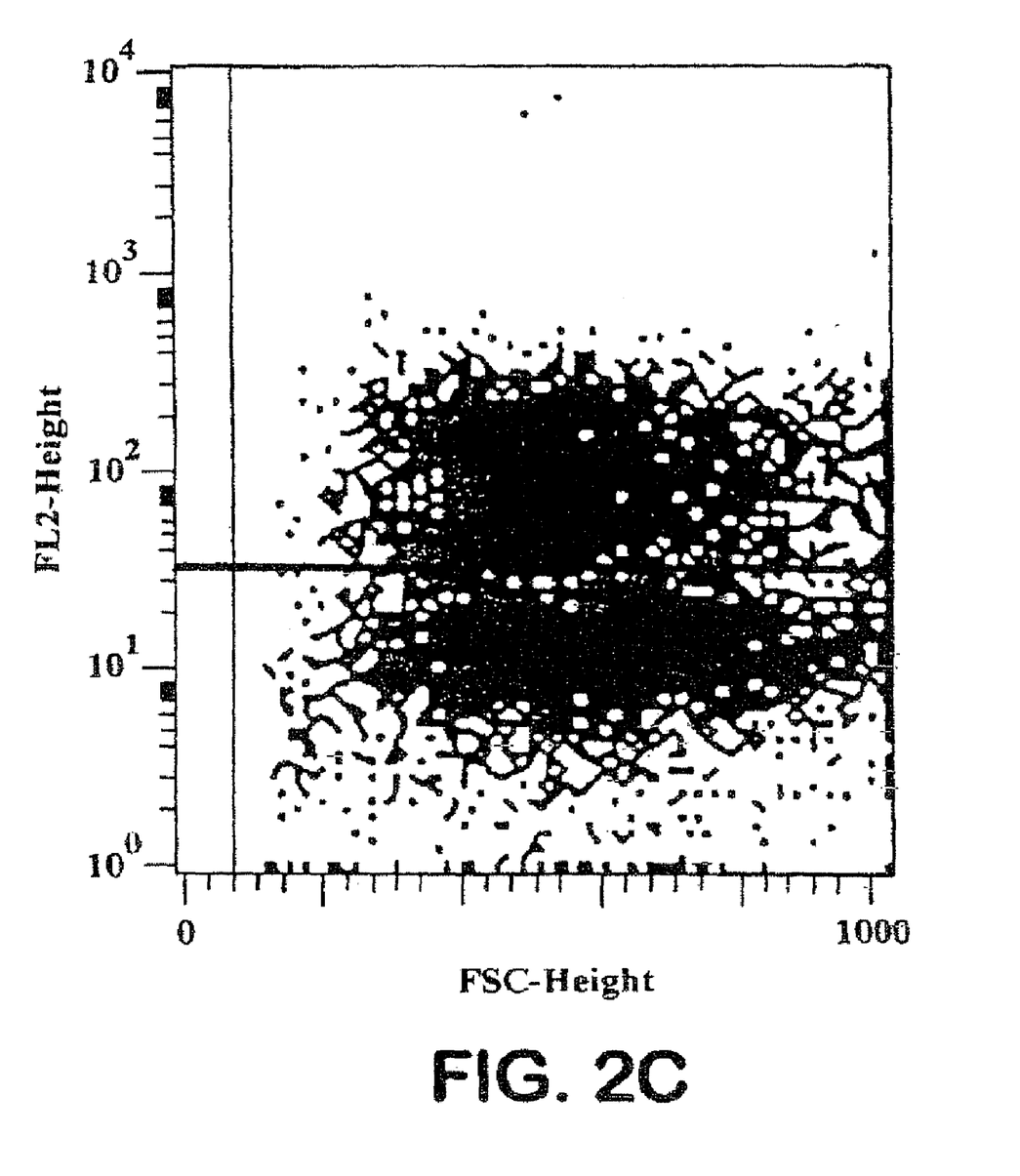

The read-out was the staining of a mixture of CD28 transfected and untransfected L929 tumour cells. FIG. 2 shows that the CMY-2 monoclonal antibody isolated in this way distinguishes transfected and untransfected cells by differences in the fluorescence intensity. The differential screening for antibodies against human-CD28 was done as follows. 50 .mu.l each of supernatant of cultivated cell hybridoma were removed and incubated for 15 min with a mixture of L929 cells and L929-CD28 transfectants. After washing, the cells were stained with DaMIg-PE. Part A shows the negative check. The cells were only incubated with DaMIg-PE. Part B shows the coloration with a supernatant which was slightly positive, but shows no difference in the two cells. Part C shows the cells stained with a supernatant of CMY-2.

In experiments which have not been portrayed, peripheral blood cells of man were stained with the newly isolated CMY-2 and the "classical", CD28-specific antibody 9.1. An identical expression pattern was found on the sub-populations of human blood cells.

To sum up, the experiments show that CMY-2 is a human CD28-specific antibody.

CMY-2 was then tested with human T-lymphocytes from peripheral blood enriched to about 80% for classical co-stimulating and for "directly" stimulating activity. The T cell proliferation was measured by adding .sup.3H-thymidin between the 2.sup.nd and 3.sup.rd day of the culture. The following results were achieved:

TABLE-US-00001 Co-stimulation: Unstimulated cells 276 cpm CD3-specific antibodies 3111 cpm CD3-specific antibodies+CMY-2 51676 cpm Direct stimulation: Solid-phase anti-mouse Ig 379 cpm Solid-phase anti-mouse Ig+control mAk 258 cpm Solid-phase anti-mouse Ig plus CMY-2 19115 cpm As an explanation: Anti-CD3 ensures T cell receptor stimulation (CD3 is a part of the TCR complex). CMY-2 was used in the form of an uncleaned culture supernatant (50% final volume). Experience has shown that the effective mAk concentration to be expected is sub-optimal for a direct activation, but sufficient for the co-stimulation. The experiment shows that CMY-2 has directly activating properties.

Hybridoma cells according to the invention which produce CMY-2 have been deposited with the DMSZ, the German Collection of Micro-organisms and Cell Cultures, Mascheroder Weg 1b, D-38124 Braunschweig, under number DSM ACC2533 on May 20, 1998.

EXAMPLE 2

In this example, the immune-modulating effect of "direct" CD28-specific monoclonal antibodies is explained in more detail. The objective of the experiments is proof of the lead cytokines of the TH2 cells, IL-4 and IL-10, as a result of the direct activation in vitro and in vivo. IL-4 is decisive for the cooperation of the TH2 cells with B lymphocytes, for the differentiation of further CD4 T cells to TH2 cells and thus the polarisation of the immune system away from the inflammation and towards the humoral immune reaction, and IL-10 is the central factor for the suppression of inflammatory (TH1) reactions. Only the more important results of the in vivo treatment of rats have been portrayed. In vitro, even clearer effects were found.

Figure 3:
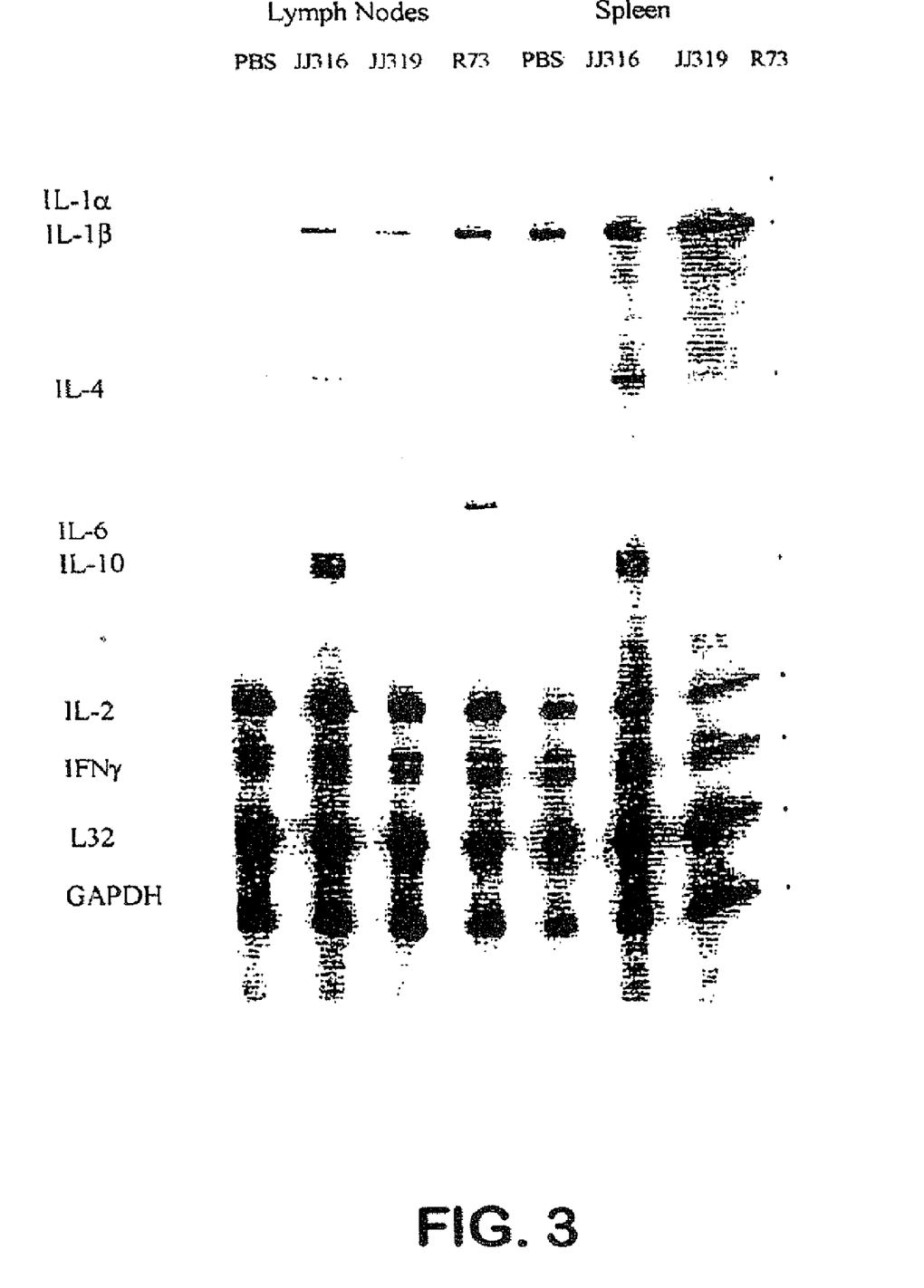
FIG. 3 shows results of an RNAse protection test.

FIG. 3 shows the expressed cytokine profile of lymphatic nodes and spleen cells of young LEW rats three days after i.p. injection of the directly activating mAk JJ316, the co-stimulator JJ319, the TCR-specific mAk R73 or the vehicle PBS.

The figure shows a so-called RNAse protection test, in which radioactively marked antisense mRNA samples are protected against the decomposition of added RNAse. These go onto bands defined on the gel and make it possible to have a good overview of the expressed cytokine profile on the mRNA level of a tissue at a glance. The two smallest fragments, L32 and GADPH, are "household genes", the identical expression of which is used for the check of equally large amounts of RNA used in the individual cases. The test was carried out with a kit commercially available from the firm of Pharmingen.

JJ316, not JJ319 or R73, massively induce IL-10 and, to a lesser extent, IL-4 mRNA. The effects are especially clear in the spleen, but are also visible in lymph nodes.

Figure 4A:
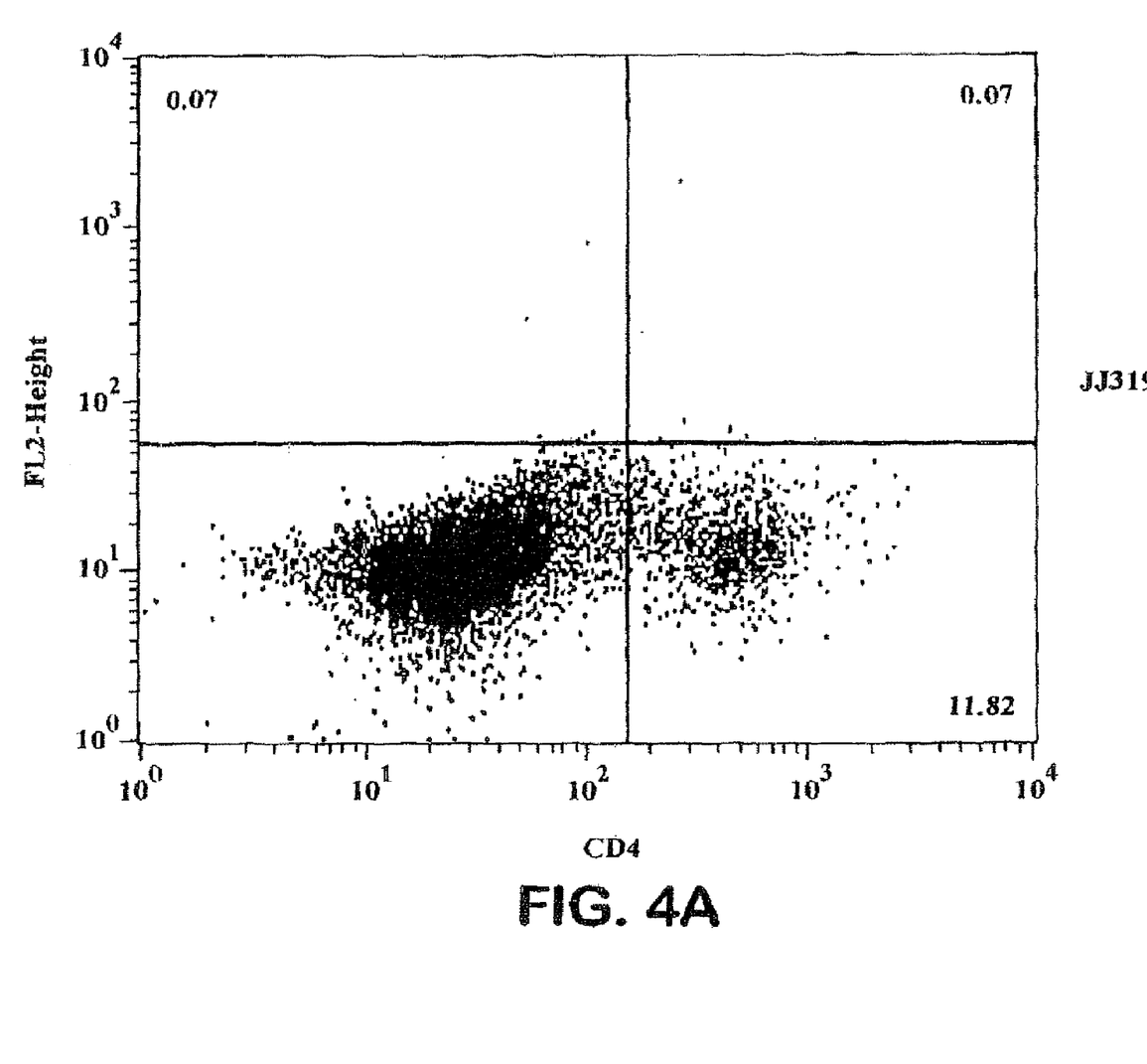
FIGS. 4A-4B show flow-cytophotometric data.
Figure 4B:
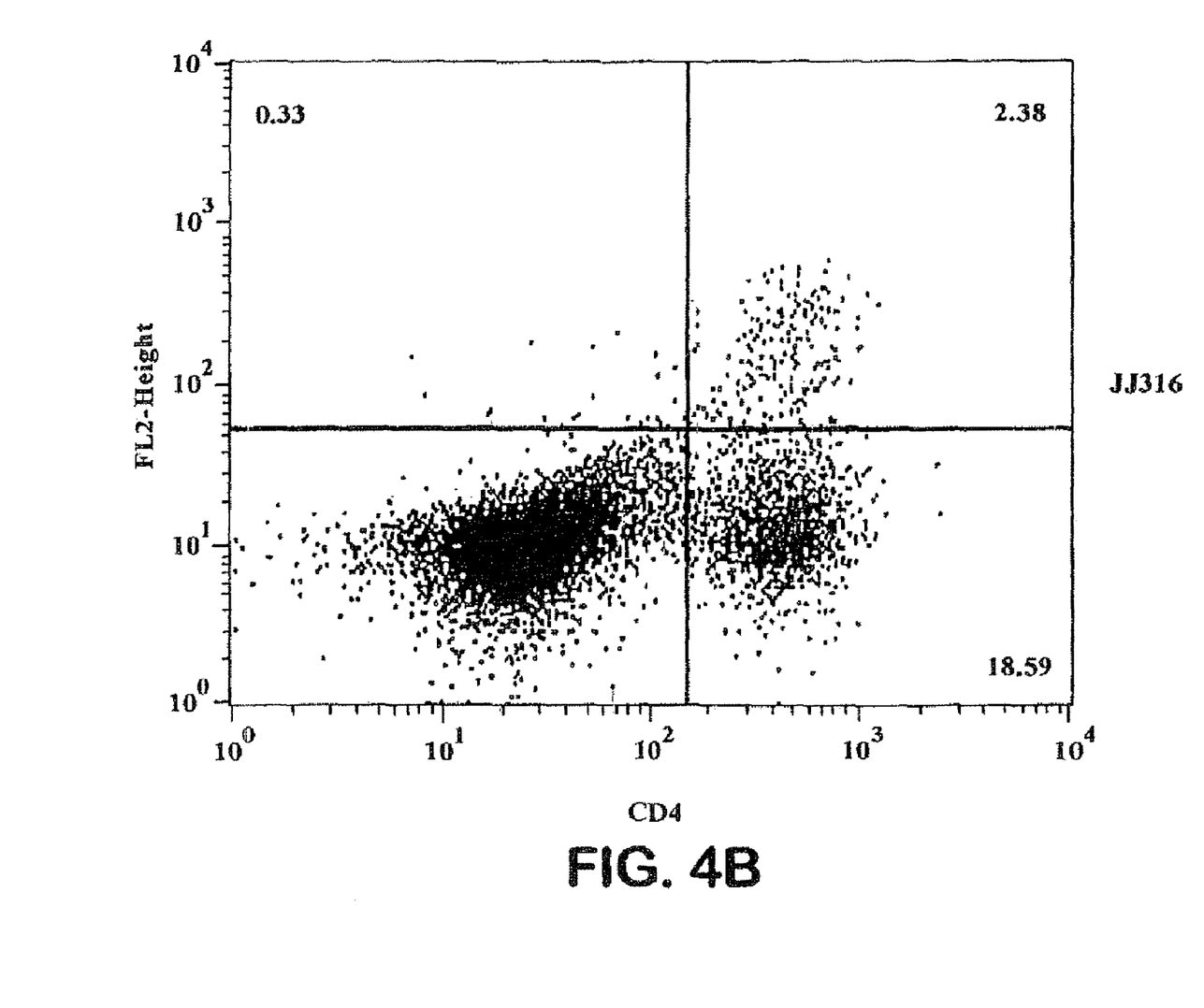

In FIG. 4, the cytokine IL-4 on a protein and simultaneously on a single-cell level is proven by flow-cytophotometric analysis. For this purpose, the cells are firstly stained with mAk against the surface molecule CD4, then fixed and made permeable, with the result that the IL-4 protein can be proven in a subsequent cytoplasmatic staining with an IL-4-specific mAk which is marked with a second fluoride chrome. The evaluation is done in a flow-cytophotometer, each point representing a cell. The quadrants inserted represent the borders between the background and a positive reaction. The methods are also described in great detail in the catalogue of the firm of Pharmingen.

As FIG. 4 shows, the injection of the mAk JJ316, but not that of the classical costimulator JJ319, induces the production of IL-4 in a substantial share of the isolated CD4 T cells.

Figure 5:
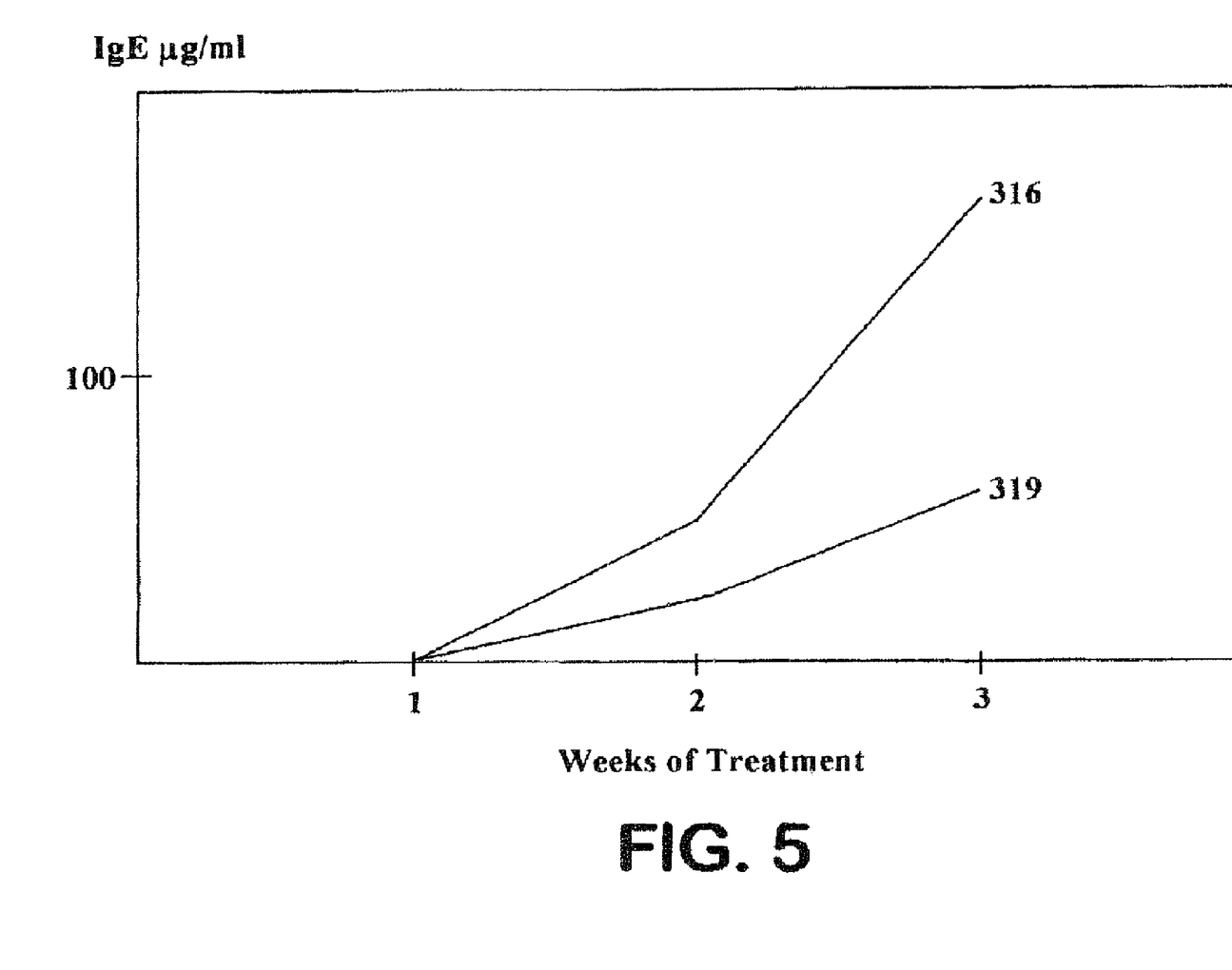
FIG. 5 shows IL-4 production results.

In FIG. 5, a biological effect of the increased IL-4 production is shown: the level of detectable antibodies of the IGE class clearly rises as a result of the treatment with mAk JJ316 and proves the in vivo effectivity of the IL-4 secretion induced by "direct" CD28-specific monoclonal antibodies.

Figure 6:
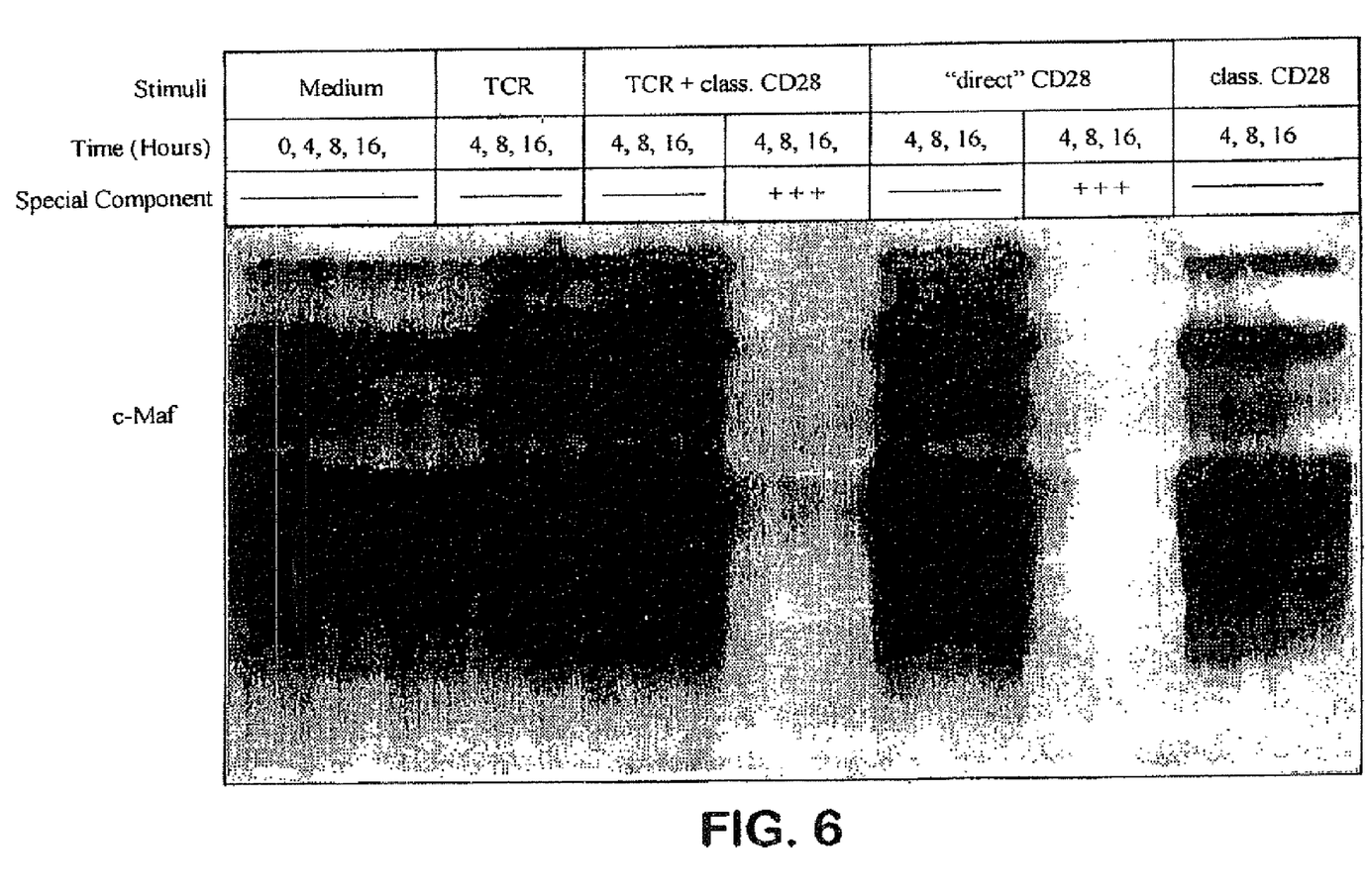
FIGS. 6 and 7 show EMS assay data.
Figure 7:
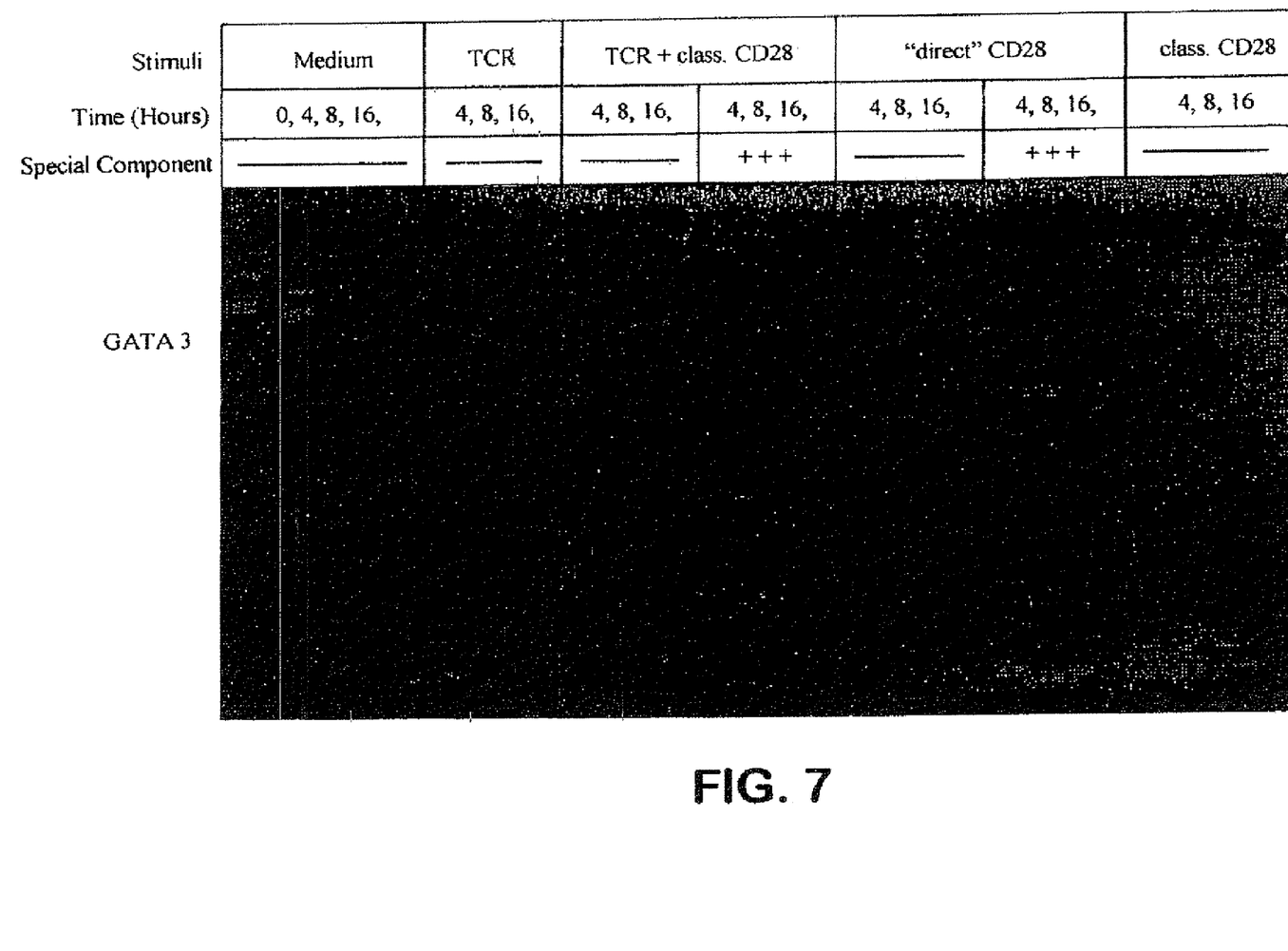

FIGS. 6 and 7 show so-called EMSAs (Electrophoretic Mobility Shift Assays) as a proof of the induction of transcription factors which support the development of anti-inflammatory TH2 cells. The technique is as follows. T cells are stimulated in vitro for differing lengths of time, then the proteins from the cell cores are put into solution and incubated with a radioactively marked short gene probe, the sequence of which they should recognise as transcription factors. After the incubation, the mixture is separated on a poly-acrylamide gel. The unbound marked gene probe exudes from the gel at the bottom (cannot be seen here). Bands such as those portrayed here are partly non-specific (exist everywhere) or are selectively induced (strong, weak signals, depending upon the stimulus).

The following becomes clear from looking at FIGS. 6 and 7. Both with a GATA3-specific as well as with a c-Maf-response-element-specific sample, increased induction in co-stimulation (TCR and classical CD28) as well as direct stimulation ("direct" CD28) can be seen in comparison with the stimulation only via the T cell receptor (TCR). To sum up, it can be stated that stimulation of the CD28 molecule supports the expression of these transcription factors in the cell core and that this is also possible without TCR stimulation by direct CD28 stimulation. Reference is made to Current Opinion in Immunology 1997, 9:776-781, for the importance of these factors for the differentiation of TH2 cells.

The interconnections for the immune-regulatory and immune-modulating effect of "direct" CD28-specific monoclonal antibodies with regard to the formation of TH1 and/or TH2 cells explained above in detail consequently make them especially suited for the production of medicine for the treatment of such immune reactions of independent diseases. Principally, these are all the allergic-inflammatory and auto-immune-inflammatory clinical pictures. The former include, for example, the inflammatory diseases of the intestines summarised under the designation "Inflammatory Bowel Disease" (IBD) and contact dermatitis. The latter includes Type I diabetes and multiple sclerosis. It can also be expected that a strong stimulation of the human CD28 molecule by monoclonal antibodies according to the invention will be in a position to cure T cells infected by HIV I. In this way, chemokine receptors used by the viruses as cellular co-receptors can be eliminated an the production of chemokines, which bind on such receptors and thus block them for HIV I viruses, can be induced.

EXAMPLE 3

Figure 8:
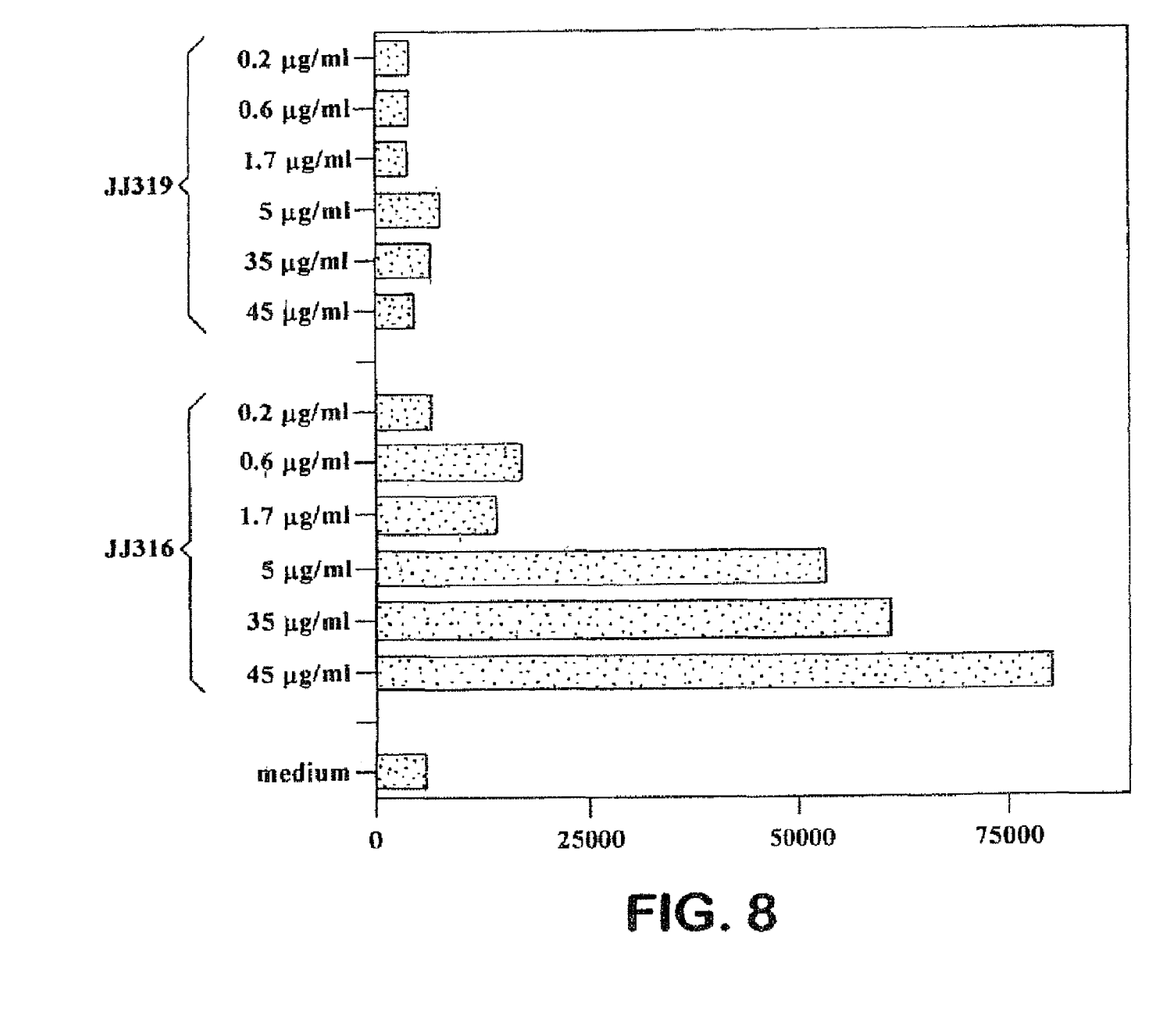
FIG. 8 shows proliferative effects from antibody JJ316.

FIG. 8 shows the proliferative reaction of unseparated lymphatic node cells of rats to the "directly" stimulating CD28-specific monoclonal antibody (JJ316) and the lack of such a reply in the use of a "classical" CD28-specific monoclonal antibody (JJ319). The cells were cultivated for 2 days in 0.2 ml of medium (RPMI 1640, available for GIBCO/BRL, containing 5% FCS [fetal calf serum]) in presence or absence of the above mentioned additives with a density of 1 million cells per ml in a gassed incubator. The cell division activity was determined by the addition of radioactively marked thymidin (1 .mu.Ci/insertion for 16 hours, 1 Ci-37 GBq, determination with .beta. detector).

Unlike published results (Siefken et al., Cellular Immunology, 1997, 176: 59-65), this result shows that, for the T cell activation by directly activating CD28-specific monoclonal antibodies, it is not necessary to crosslink them artificially by means of a second antibody. Rather, the presence of non-T cells from lymphoid organs, viz. from B lymphocytes and so-called accessory cells, is sufficient in order to make a direct activation by solubly added CD28-specific monoclonal antibodies possible. This probably happens through the binding of the monoclonal antibodies to so-called Fc receptors of these non-T cells. This result is an important precondition for the therapeutic use of "directly" stimulating CD28-specific monoclonal antibodies, in which an artificial crosslinking with anti-immunoglobulin antibodies in the entire organism is not practicable.

EXAMPLE 4

Figure 9:
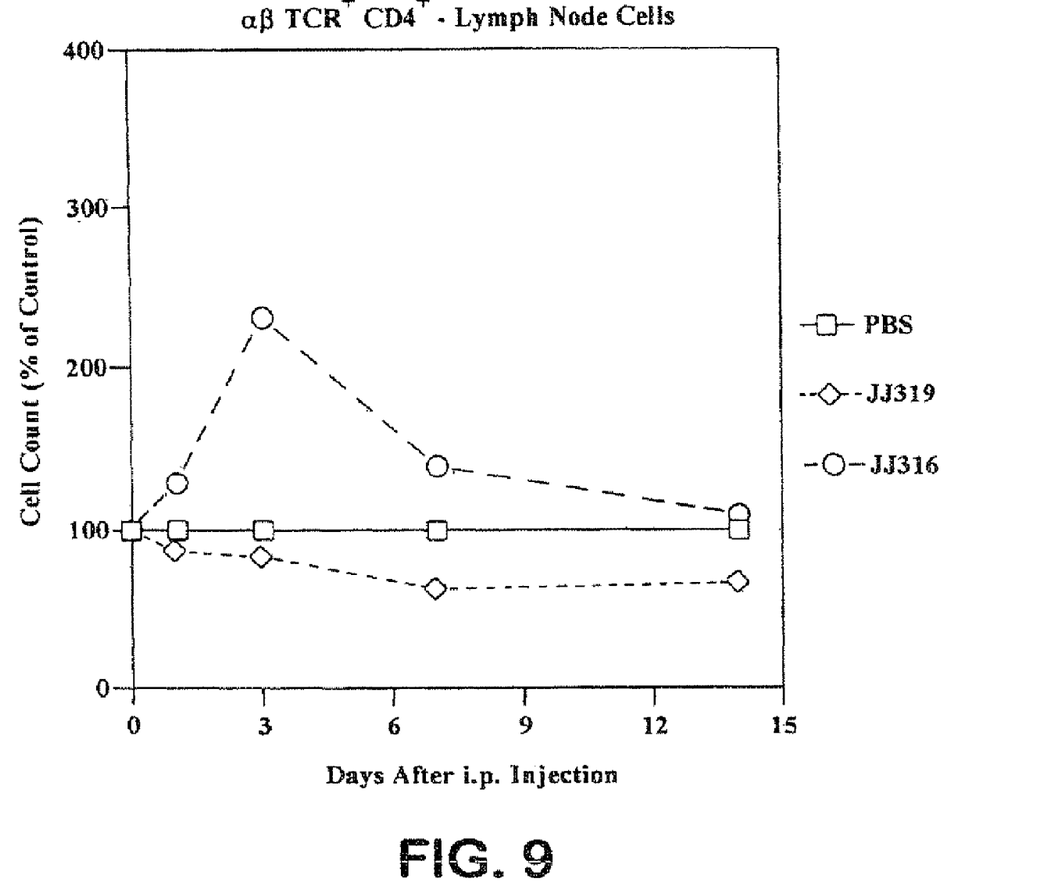
FIG. 9 shows results fo CD28-antibody activation.

"Directly" activating CD28-specific monoclonal antibodies lead to an increase in the number of CD4 T cells in an intact organism. FIG. 9 shows this for lymphatic nodes in rats which had been given 1 mg of the "directly" stimulating CD28-specific monoclonal antibody (JJ316) or of the "classical" CD28-specific monoclonal antibody (JJ319) on day 0. With directly activating monoclonal antibodies according to the invention with a specificity for human-CD28 and their ability to stimulate the proliferation of T-lymphocytes, totally analogous effects were achieved. This can then be particularly applied in situations in which the share of CD4 T cells has been pathologically reduced and is to be brought back up towards the normal level again. Such situations can particularly be found in the clinical picture of AIDS and after chemotherapy and bone marrow transplantations. In this example, the number of CD4 T cells is only temporarily increased; this is due to the fact that healthy animals were treated with normal CD4 T cells. The "surplus" cells resulting from the proliferation stimulation are reduced by homeostatic mechanisms.

EXAMPLE 5

Figure 10:
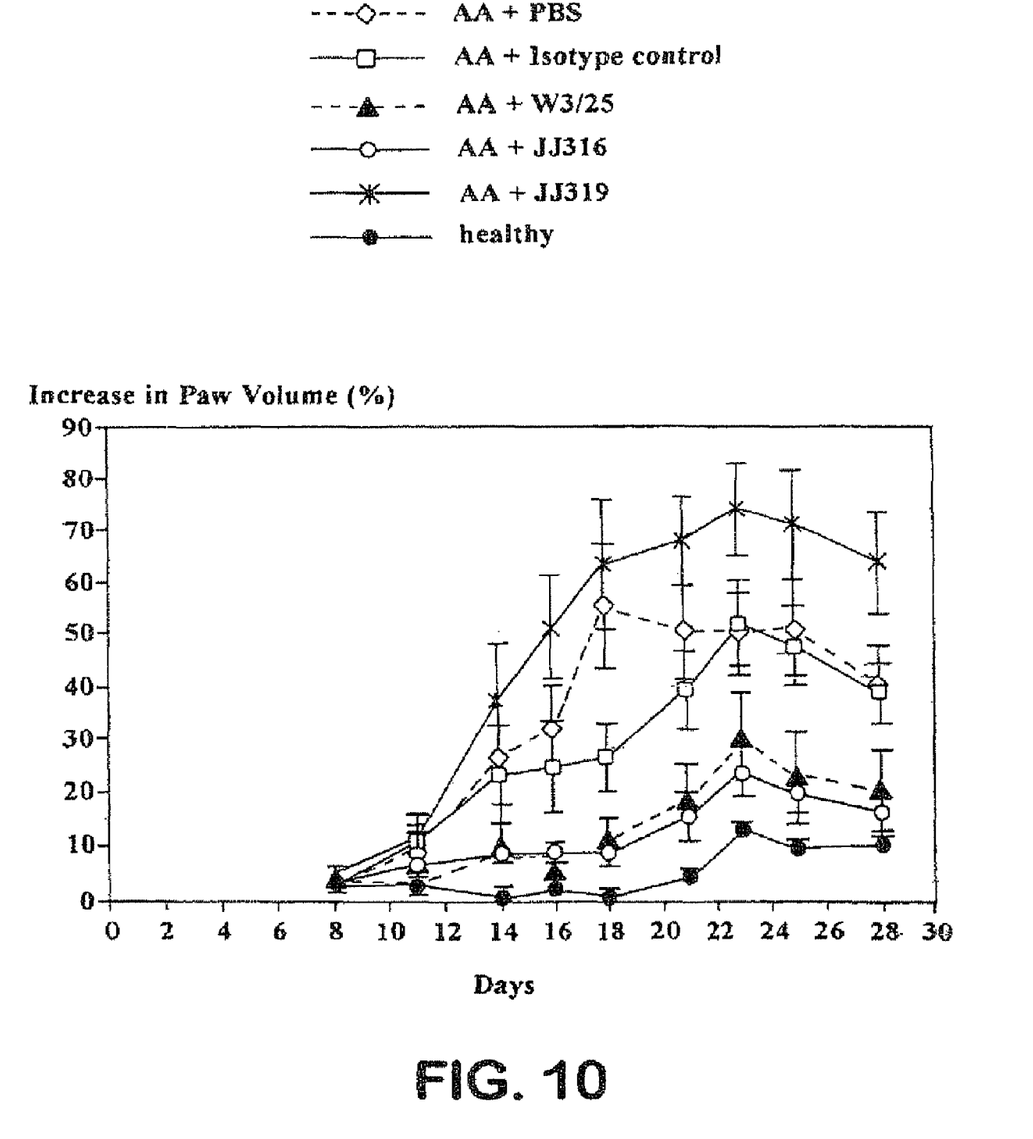
FIGS. 10 and 11 show results of an adjuvant arthritis test.
Figure 11:
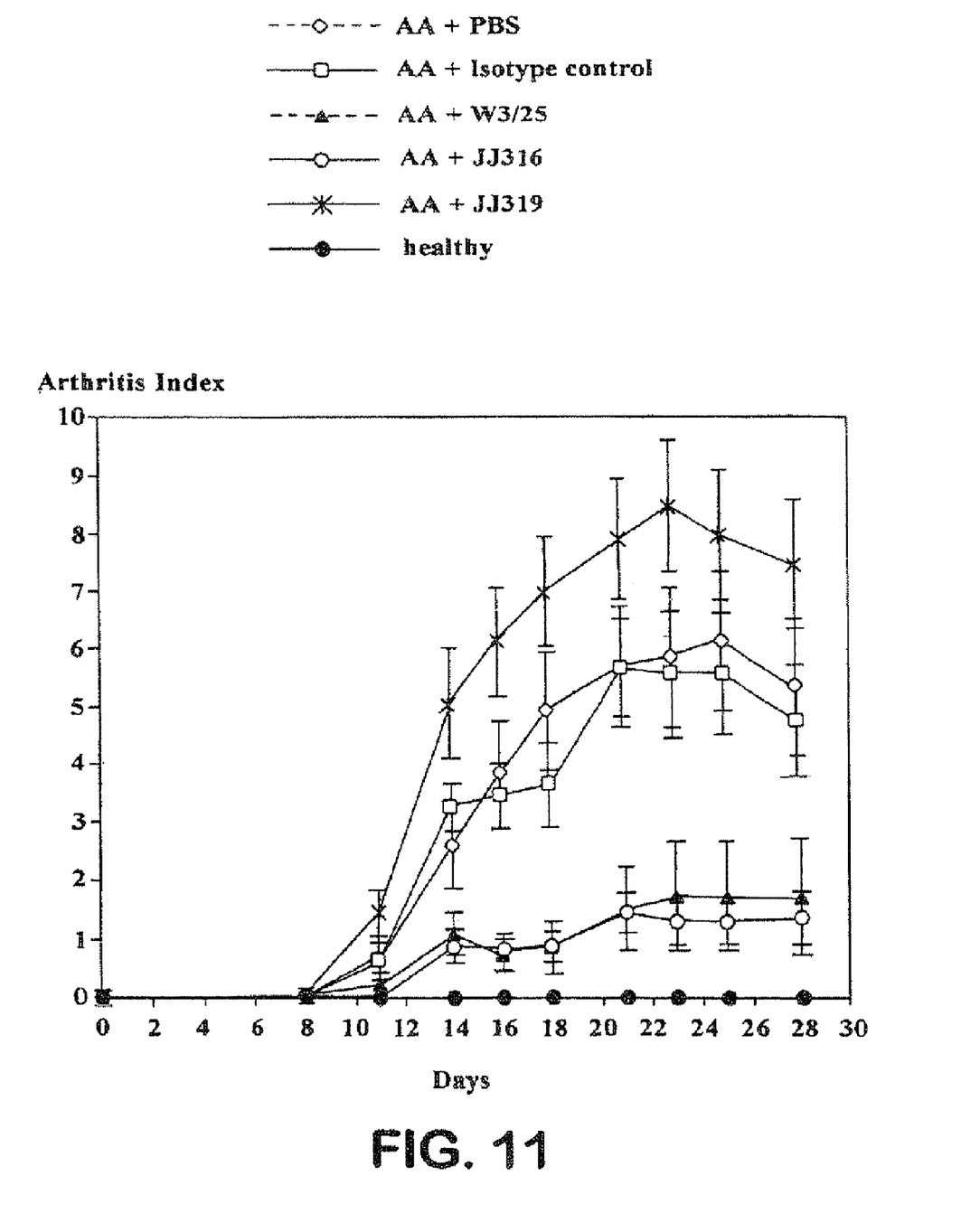

As can be expected from the deductions made above from FIGS. 5-7, directly activating CD28-specific monoclonal antibodies can be used therapeutically, inter alia to prevent inflammatory auto-immune reactions. FIG. 10 shows an experiment on this for the so-called Adjuvans Arthritis in rats, a model system for certain forms of rheumatoid arthritis in humans. "Paw volume increase" shows the increase in the volume of the paw. "Healthy" data points show figures for healthy animals. As an isotype control, a monoclonal antibody of the same immunoglobin class with specificity for an irrelevant human cell surface molecule was used. AA stands for Adjuvans Arthritis. PBS stands for "Phosphate-buffered saline". W3/25 stands for a monoclonal antibody with specificity for the CD4 molecule of rats. The Adjuvans Arthritis is mediated by so-called TH1 cells. TH1 cells result from resting CD4 T cells in the course of the activation under the influence of certain soluble factors of the immune system, so-called cytokines. The counterparts of the TH1 cells are the TH2 cells, which have an antiinflammatory effect and the induction of which is controlled by other cytokines. In the experiment shown in FIGS. 10 and 11, the induction of the Adjuvans Arthritis was almost completely suppressed by the "directly" activating CD28-specific monoclonal antibody JJ316, measured on the joint swelling (FIG. 10) and the arthritic index (FIG. 11) after immunisation with mycobacteria in Adjuvans. The "classical" CD28-specific monoclonal antibody (JJ319) had the opposite effect, i.e. it deteriorated the clinical picture. From this, it can be seen, also for use in humans, that the immune reaction can be influenced by the application of conventional or "directly" stimulating CD28-specific monoclonal antibodies according to the invention, here in the sense of an "immune deviation" to TH1 or TH2. In other words, monoclonal antibodies according to the invention, but also "classical" monoclonal antibodies which are specific for human-CD28 (and/or are available by immunisation with T cells) cause an immune modulation. Such a purpose of application of "classical" monoclonal antibodies is also not known.

Therefore, the invention also affects the use of monoclonal antibodies specific against human-CD28 (available according to the above mentioned principal modes of procedure in immunisation with T cell lines or non-T cell lines expressing human-CD28) for the production of medicines for the modulation of immune reactions, viz. immune suppression (for example with human-CD28 analogues to JJ319) or immune reinforcement (for example with human-CD28 analogues to JJ316 such as CMY-2).

I claim:

1. A method for antigen-non-specifically activating a subgroup of human T lymphocytes, comprising contacting at least one human T lymphocyte with a human-compatible monoclonal antibody which is specific for human CD28 and which is capable of activating said human T-lymphocytes without occupancy of an antigen receptor of said human T-lymphocyte.

* * * * *